United States Patent
Tamura et al.

(10) Patent No.: US 9,901,489 B2
(45) Date of Patent: Feb. 27, 2018

(54) ABSORBENT ARTICLE

(71) Applicant: UNICHARM CORPORATION, Ehime (JP)

(72) Inventors: Tatsuya Tamura, Kanonji (JP); Yuki Noda, Kanonji (JP); Akira Hashino, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 15/323,031

(22) PCT Filed: Apr. 16, 2015

(86) PCT No.: PCT/JP2015/061738
§ 371 (c)(1),
(2) Date: Dec. 29, 2016

(87) PCT Pub. No.: WO2016/002304
PCT Pub. Date: Jan. 7, 2016

(65) Prior Publication Data
US 2017/0135866 A1 May 18, 2017

(30) Foreign Application Priority Data
Jun. 30, 2014 (JP) .................................. 2014-135394

(51) Int. Cl.
*A61F 13/00* (2006.01)
*A61F 13/47* (2006.01)
(Continued)

(52) U.S. Cl.
CPC .......... *A61F 13/4704* (2013.01); *A61F 13/53* (2013.01); *A61F 13/539* (2013.01);
(Continued)

(58) Field of Classification Search
CPC .... A61F 13/4704; A61F 13/53; A61F 13/539; A61F 2013/530131; A61F 2013/53908;
(Continued)

(56) References Cited

U.S. PATENT DOCUMENTS 9,216,118 B2 * 12/2015 Roe .................... A61F 13/49001
2006/0069371 A1 3/2006 Ohashi et al.
(Continued)

FOREIGN PATENT DOCUMENTS

| EP | 2835120 A1 | 2/2015 |
| GB | 2186233 A | 8/1987 |
| JP | 10-99372 A | 4/1998 |
| JP | 10099372 A * | 4/1998 |
| JP | H1099372 A | 4/1998 |

(Continued)

*Primary Examiner* — Tatyana Zalukaeva
*Assistant Examiner* — Jessica Arble
(74) *Attorney, Agent, or Firm* — Hauptan Ham, LLP

(57) ABSTRACT

This absorbent article has sufficient pliability even when an absorbent body is bonded to a transport material, a wrap material, etc., and is pleasant to wear. In this absorbent article (1), an absorbent body (4) includes at least a hydrophilic fiber-containing hydrophilic fiber layer (5) having multiple non-through slits (8), and in the surface opposite of the surface having the slits (8), the hydrophilic fiber layer (5) has multiple recesses (9) in positions corresponding to the multiple non-through slits (8) in the thickness direction of the absorbent article (1).

13 Claims, 2 Drawing Sheets

(51) Int. Cl.
*A61F 13/53* (2006.01)
*A61F 13/539* (2006.01)

(52) U.S. Cl.
CPC ............ *A61F 2013/530131* (2013.01); *A61F 2013/53908* (2013.01)

(58) Field of Classification Search
CPC .................. A61F 13/537; A61F 13/538; A61F 13/15642; A61F 13/15723; A61F 13/15731; A61F 13/15747; A61F 13/49001; A61F 13/53409; A61F 13/53717; A61F 13/53747
See application file for complete search history.

(56) References Cited

U.S. PATENT DOCUMENTS

| | | |
|---|---|---|
| 2009/0062760 A1 | 3/2009 | Wright et al. |
| 2010/0069868 A1 | 3/2010 | Noda et al. |
| 2013/0184665 A1* | 7/2013 | Kato ................ A61F 13/4704 604/374 |

FOREIGN PATENT DOCUMENTS

| | | |
|---|---|---|
| JP | 2006-95156 A | 4/2006 |
| JP | 2007-97954 A | 4/2007 |
| JP | 2007097954 A | 4/2007 |
| JP | 2008095156 A | 4/2008 |
| JP | 2008-229214 A | 10/2008 |
| JP | 2009-131417 A | 6/2009 |
| JP | 2011-136015 A | 7/2011 |
| WO | 2013/150921 A1 | 10/2013 |

\* cited by examiner

ABSORBENT ARTICLE

RELATED APPLICATIONS

The present application is a National Phase of International Application Number PCT/JP2015/061738, filed Apr. 16, 2015, which claims priority to Japanese Application Number 2014-135394, filed Jun. 30, 2014.

TECHNICAL FIELD

The present invention relates to an absorbent article.

BACKGROUND ART

Absorbent articles such as sanitary napkins and incontinence pads preferably deform along the shape of the body of the wearer in order to minimize leakage of excreta, such as menstrual blood. As an example of such an absorbent article that can deform along the shape of the body, PTL 1 discloses an absorbent article wherein the absorbent body has folding sections with lower flexural rigidity than the average flexural rigidity of the absorbent body, and with lower flexural rigidity than the adjacent regions. Since the absorbent article disclosed in PTL 1 flexibly deforms around the folding sections formed in the absorbent body as origins, it easily fits along the body shape of the wearer and can exhibit a soft feel during use.

PTL 2 discloses an absorbent article wherein the absorbent body has regions with increased density and basis weight in sections thereof, and further has sections with increased absorbent body density locally within the regions of increased density and basis weight, with recesses corresponding to those sections. Because the absorbent article disclosed in PTL 2 has an absorbent body with a plurality of recesses of increased density, the absorbent body is capable of flexible deformation.

Also, PTL 3 discloses an absorbent article wherein the upper layer absorbing element is composed of an upper layer absorbent body containing synthetic fibers and a covering sheet comprising a nonwoven fabric of synthetic fibers that encloses the upper layer absorbent body, the upper layer absorbing element having a plurality of crossing grooves formed crossing the widthwise direction of the upper layer absorbent body, at intervals in the lengthwise direction, by embossing from the front side of the covering sheet. The absorbent article disclosed in PTL 3 has a structure in which the upper layer absorbent body and the covering sheet made of a nonwoven fabric that encloses the upper layer absorbent body, are integrated by embossing, and since folding takes place from the embossed grooves, it is capable of bending in a smooth manner along the rounded curves of the body.

CITATION LIST

Patent Literature

[PTL 1] Japanese Unexamined Patent Publication No. 2008-229214
[PTL 2] Japanese Unexamined Patent Publication No. 2009-131417
[PTL 3] Japanese Unexamined Patent Publication No. 2011-136015

SUMMARY OF INVENTION

Technical Problem

However, while the absorbent articles disclosed in PTLs 1 and 2 have the folding sections or recesses formed in the absorbent body that serve as origins for folding of the absorbent body, when the absorbent body is attached to a transport material or wrap material, these origins become stretched due to tension of the transport material or the like, potentially preventing the desired flexibility from being satisfactorily exhibited. Moreover, since the absorbent article disclosed in PTL 3 has the embossed grooves formed by simultaneous embossing of the upper layer absorbent body and the covering sheet, the covering sheet becomes stretched between the embossed grooves, potentially impairing the flexibility.

It is therefore an object of the present invention to provide an absorbent article that has sufficient flexibility even when the absorbent body is attached to a transport material or wrap material, and that can exhibit a comfortable feel during wear.

Solution to Problem

In the absorbent article of the present invention, the absorbent body includes at least a hydrophilic fiber layer having a plurality of non-through slits and including hydrophilic fibers, the hydrophilic fiber layer having, on the side opposite the side with the slits, a plurality of recesses at locations corresponding to the plurality of non-through slits, in the thickness direction of the absorbent article.

Since the absorbent body in the absorbent article of the present invention includes at least a hydrophilic fiber layer having a plurality of non-through slits and the hydrophilic fiber layer has, on the side opposite the side with the slits, a plurality of recesses at locations corresponding to the plurality of non-through slits, in the thickness direction of the absorbent article, the absorbent body can be easily deformed from the plurality of recesses as origins, and therefore the absorbent article has sufficient flexibility and a comfortable feel during wear can be provided.

Advantageous Effects of Invention

According to the present invention it is possible to provide an absorbent article having sufficient flexibility and exhibiting a comfortable feel during wear.

DESCRIPTION OF EMBODIMENTS

Preferred embodiments of the absorbent article of the present invention will now be described in detail with reference to the accompanying drawings.

Figure 1:
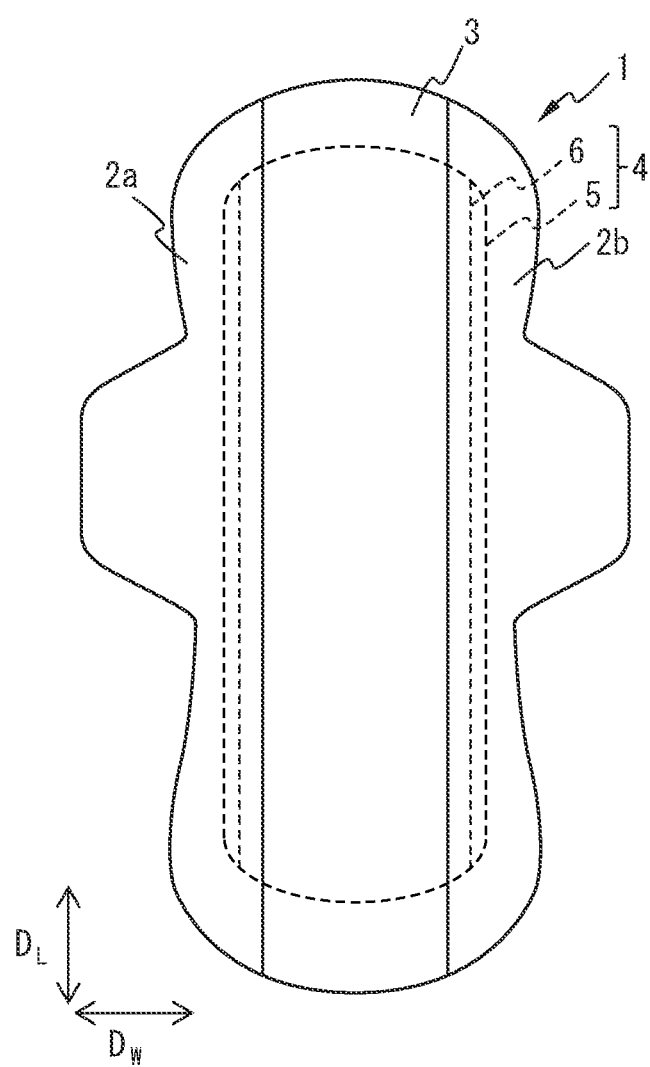
FIG. 1 is a plan view of an absorbent article according to an embodiment of the present invention.

FIG. 1 is a plan view of a sanitary napkin 1, as an absorbent article according to an embodiment of the present invention. As shown in FIG. 1, the napkin 1 has a longitudinal shape with a lengthwise direction $D_L$ and a widthwise direction $D_W$ orthogonal to the lengthwise direction $D_L$, in a plane view. The napkin 1 is constructed by different members including a pair of left and right liquid-impermeable side section sheets 2a, 2b situated on the side of the wearer's skin, a liquid-permeable top sheet 3 comprising a nonwoven fabric or a liquid-permeable plastic film or the like, situated on the clothing side of the side section sheets 2a, 2b, a liquid-impermeable back sheet (not shown) situated on the clothing side (i.e., the side opposite from the skin side), and an absorbent body 4 situated between the top sheet 3 and the back sheet, that absorbs and retains body fluids, such as menstrual blood. Furthermore, the absorbent body 4 in the napkin 1 of this embodiment has a two-layer layered structure comprising a hydrophilic fiber layer 5 including hydrophilic fibers, and a synthetic fiber layer 6 made of synthetic fibers, that is adjacent to the skin side of the hydrophilic fiber layer 5 and at least partially covers the hydrophilic fiber layer 5. In the absorbent article of the present invention, the absorbent body is not limited to having such a two-layer layered structure, and may have a single-layer structure or any layered structure with two or more layers, so long as it includes the aforementioned hydrophilic fiber layer.

Figure 2:
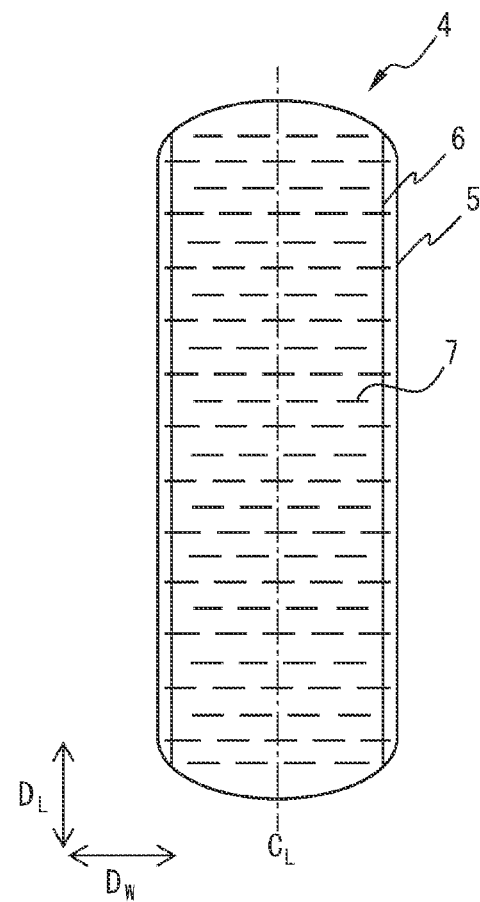
FIG. 2 is a plan view of an absorbent body to be used in an absorbent article according to an embodiment of the present invention.
Figure 3:
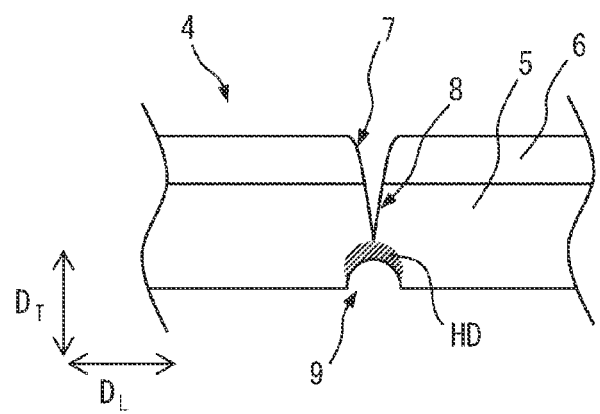
FIG. 3 is a partial cross-sectional view along the center axis line $C_L$ running in the lengthwise direction $D_L$ of the absorbent body shown in FIG. 2.

The absorbent body to be used in the absorbent article of the present invention will now be described in detail with reference to the accompanying drawings. FIG. 2 is a plan view of an absorbent body 4 to be used in an absorbent article (napkin 1) according to an embodiment of the present invention, and FIG. 3 is a partial cross-sectional view along the center axis line $C_L$ running in the lengthwise direction $D_L$ of the absorbent body 4 shown in FIG. 2. As shown in FIG. 2, for this embodiment, the absorbent body 4 has a longitudinal shape that is long in the longitudinal direction (MD direction) that matches the lengthwise direction $D_L$ of the absorbent article.

For this embodiment, the absorbent body 4 comprises a hydrophilic fiber layer 5 and a synthetic fiber layer 6 that is adjacent to the skin side of the hydrophilic fiber layer 5, and it has a two-layer layered structure. The hydrophilic fiber layer 5 used is preferably one having a superabsorbent polymer dispersed and held in a fiber structure that includes pulp, and the hydrophilic fiber layer to be used in the absorbent article of the present invention is not particularly restricted so long as it has the function of absorbing and holding body fluids such as menstrual blood, while there may also be used any desired absorbent material such as a nonwoven fabric comprising hydrophilic fibers such as cellulosic fibers, in addition to the superabsorbent polymer dispersed and held in a fiber structure including pulp. The hydrophilic fiber layer used is preferably one having the absorbent material compressed with a roll press or the like, since the rigidity of the absorbent body will be high and the absorbent body will thus be resistant to tearing during use of the absorbent article.

In the absorbent article of the present invention, the basis weight of the hydrophilic fiber layer is not particularly restricted but is preferably 100 g/m² to 500 g/m² and even more preferably 150 g/m² to 300 g/m², from the viewpoint of liquid absorption, flexibility and strength. Moreover, there is no particular restriction on the thickness of the hydrophilic fiber layer, but it is preferably 1.0 to 10.0 mm and more preferably 1.5 mm to 5.0 mm, from the same viewpoint mentioned above.

As the synthetic fiber layer 6 there may be suitably used a liquid-permeable nonwoven fabric made of synthetic fibers such as polyolefin-based fibers (for example, polyethylene or polypropylene) or polyester-based fibers (for example, polyethylene terephthalate). When a nonwoven fabric is used as the synthetic fiber layer, it will more easily retain its shape even after body fluids such as menstrual blood that have permeated the top sheet have been absorbed, and the absorbent body will be less likely to undergo deformation. The synthetic fiber layer used in the absorbent article of the present invention is not particularly restricted so long as it allows permeation of body fluids such as menstrual blood, and in addition to the aforementioned nonwoven fabric there may be used any desired fiber material such as, for example, a woven fabric made of synthetic fibers.

In the absorbent article of the present invention, the basis weight of the synthetic fiber layer is not particularly restricted but is preferably 10 g/m² to 70 g/m² and more preferably 20 g/m² to 40 g/m², from the viewpoint of liquid permeation, flexibility and strength. Also, the thickness of the synthetic fiber layer is not particularly restricted but is preferably 0.1 mm to 5.0 mm and more preferably 0.2 mm to 2.0 mm, from the same viewpoint mentioned above.

For this embodiment, at least part of the synthetic fiber layer 6 is joined with the hydrophilic fiber layer 5 by any desired adhesive, such as a hot-melt adhesive. By joining the hydrophilic fiber layer 5 and the synthetic fiber layer 6, there will be less likelihood that the hydrophilic fiber layer 5 and synthetic fiber layer 6 will separate during use of the absorbent article and result in twisting of the absorbent body 4, or tearing of the absorbent body 4 starting from the slits or notched sections described below. In addition, when the hydrophilic fiber layer and the synthetic fiber layer are joined by a hot-melt adhesive, it is possible to obtain a satisfactory feel on the skin and flexibility for the absorbent article, since protrusions and recesses or the like will not be formed in the surface of each fiber layer and especially in the surface of the synthetic fiber layer, and the joining sections are less likely to become highly rigid.

There are no particular restrictions on the means for integrating the hydrophilic fiber layer and the synthetic fiber layer, and contact bonding means such as embossing or interlocking means such as water stream entangling may also be employed in addition to the aforementioned adhesive. These means may be used alone or in combination. Particularly when embossing is used to integrate the hydrophilic fiber layer and synthetic fiber layer, the hydrophilic fiber layer and synthetic fiber layer become joined at a plurality of compressed sections formed by a plurality of embossing pins, and therefore the absorbent body becomes resistant to twisting or tearing due to separation between the hydrophilic fiber layer and synthetic fiber layer, while compressed sections with high fiber density being formed at multiple locations increases the rigidity of the absorbent body, making it even less likely for the absorbent body to tear during use of the absorbent article.

In addition, as shown in FIG. 2 and FIG. 3, the absorbent body 4 has a plurality of through notched sections 7 in the synthetic fiber layer 6, formed by penetrating the synthetic fiber layer 6 from above the synthetic fiber layer 6, and cutting into the hydrophilic fiber layer 5 to a point in the thickness direction $D_T$, and a plurality of non-through slits 8 in the hydrophilic fiber layer 5. Since the notched sections 7 are formed so as to communicate with the slits 8, at locations corresponding to each slit 8 of the hydrophilic fiber layer 5 in the thickness direction $D_T$, as shown in FIG. 3, the total depth of the notched section 7 and slit 8 described below is increased, and the absorbent body 4 folds to the side that has the notched sections 7 and slits 8 (i.e., it is valley folded to the side having the notched sections 7 and slits 8), thereby allowing the absorbent body 4 to easily deform along the body shape of the wearer, while also preventing exposure of the pulp in the hydrophilic fiber layer from the slits 8. Throughout the present description, communication between the notched sections of the synthetic fiber layer and the slits of the hydrophilic fiber layer is a state in which the notched sections and slits are spatially connected, and it does not depend on the presence or absence of close bonding between the synthetic fiber layer and the hydrophilic fiber layer.

Furthermore, for this embodiment, a plurality of straight linear notched sections 7 and slits 8 are disposed across almost the entire surface of the hydrophilic fiber layer 5 and synthetic fiber layer 6, in a plane view; however, the absorbent article of the present invention is not limited to this arrangement, and the notched sections and slits may be disposed only in one region of the hydrophilic fiber layer 5 and synthetic fiber layer 6, in a plane view.

Moreover, for this embodiment, the synthetic fiber layer 6 is disposed adjacent to the skin side of the hydrophilic fiber layer 5. If the surface of the hydrophilic fiber layer 5 with the slits 8 is on the wearer's skin side, pulp in the hydrophilic fiber layer 5 will tend to migrate when the absorbent body 4 is bent to the skin side along the body shape of the wearer when the absorbent article is worn, thereby allowing the absorbent body 4 to more easily deform along the body shape of the wearer.

In the absorbent article of the present invention, the hydrophilic fiber layer composing the absorbent body has a plurality of non-through slits, whereby it is easily folded from the slits as origins, and therefore the absorbent article can be easily deformed along the curvature of the bodily shape of the wearer. Moreover, when the synthetic fiber layer adjacent to the hydrophilic fiber layer in the absorbent body is made of a nonwoven fabric, the nonwoven fabric tends to have high rigidity under application of tension and the flexibility of the absorbent article can consequently be impaired; however, if the synthetic fiber layer has a plurality of through notched sections, the tension will be released, thereby helping to minimize high rigidity of the absorbent body and allowing the absorbent article to have excellent flexibility.

The lengths of the straight linear notched sections and slits in the absorbent article of the present invention are not particularly restricted, but may be 3 mm to 50 mm and are preferably 5 mm to 15 mm. If the lengths of the notched sections and slits are 3 mm or greater, the absorbent body will more easily fold from the slits as origins, allowing the absorbent article to be easily deformed along the curvature of the body shape of the wearer. If the notched section and slit lengths are 50 mm or smaller, the notched sections and slits will not open and tear when the absorbent body has been subjected to external pressure in the widthwise direction $D_W$, making it possible to ensure durability for the absorbent article.

The depths of the slits are not particularly restricted but may be, for example, 0.05 mm to 5.0 mm and preferably 0.1 mm to 3.0 mm, from the viewpoint of easier folding of the absorbent body. Throughout the present description, the slit depth refers to the distance between the flat section along the surface of the hydrophilic fiber layer, and the maximum depth of the slit, and specifically, it represents the depth determined by the following measuring method. (1) The absorbent body including the hydrophilic fiber layer with slits is cut on a plane crossing perpendicularly with the direction in which the slits extend. (2) The cross-section of the cut absorbent body is observed with an electron microscope such as a scanning electron microscope, and the thickness (mm) is measured at the thickest section between any two adjacent slits (hereunder referred to as the "thickest section"). (3) The thickness (mm) at the thickest section is measured at 10 arbitrary points, and the mean value is recorded as the average thickness (mm) at the thickest section. (4) Using an electron micrograph or image, with the absorbent body mounted on a horizontal plane with the side opposite the slit-bearing side of the absorbent body facing downward, the distance (mm) from an imaginary reference surface to the maximum depth of the slit is measured, assuming a flat section comprising the section in contact with the horizontal plane as an imaginary bottom face, and assuming a flat section parallel to the imaginary bottom face, the flat section being located at a position where the distance from the bottom face matches the average thickness of the thickest section, as the imaginary reference surface. (5) The distance (mm) from the imaginary reference surface to the maximum depth of the slit is measured at 10 arbitrarily selected slits, and the mean value is recorded as the slit depth (mm).

For this embodiment, each of the plurality of notched sections 7 and slits 8 extends in the transverse direction (CD direction) perpendicular to the longitudinal direction of the absorbent body 4 (i.e., the lengthwise direction $D_L$ of the absorbent article), or in other words, in the direction parallel to the widthwise direction $D_W$ of the absorbent article, in a plane view. When the plurality of notched sections and slits extend in this direction, the absorbent body will more easily bend in the lengthwise direction $D_L$ of the absorbent article, so that the absorbent article will easily deform with the sections of large curvature of the bodily shape of the wearer, and it will be possible to further improve the fitting property of the absorbent article for the wearer.

Moreover, for this embodiment, the plurality of notched sections 7 and slits 8 are disposed in a zigzag manner across almost the entire surface of the hydrophilic fiber layer 5 and synthetic fiber layer 6, in a plane view. When the plurality of notched sections and slits are thus disposed, regions of high rigidity where the notched sections and slits are not present in the absorbent body are no longer formed continuously in the lengthwise direction $D_L$ of the absorbent article, thereby allowing the absorbent article to be deformed more easily. Moreover, this effect is not limited to the aforementioned zigzag arrangement, and for example, it may be obtained by arranging the plurality of slits so that adjacent slits in the lengthwise direction $D_L$ of the absorbent article have constantly overlapping sections in the lengthwise direction $D_L$.

Also, as shown in FIG. 2, the absorbent article of the present invention preferably has no slits or notched sections at both edge sections in the widthwise direction $D_W$ (i.e., both edge sections in the widthwise direction $D_W$ of the absorbent body) in the fiber layer of either the hydrophilic fiber layer or synthetic fiber layer having the greater width (i.e., the longer length in the widthwise direction $D_W$) (or both fiber layers, if the widths of the hydrophilic fiber layer and synthetic fiber layer are the same). If slits are or notched sections are not present at both edge sections of the absorbent body, it will be possible to ensure the prescribed strength at both edge sections, and thus the absorbent body will be resistant to tearing even when friction or the like has been produced between both edge sections in the widthwise direction $D_W$ of the absorbent article, and the thigh-surrounding areas of the wearer.

The means for forming the plurality of notched sections and slits is not particularly restricted so long as the notched sections and slits are formed at corresponding locations in the thickness direction of the absorbent body, and any desired means may be employed. For example, the plurality of notched sections and slits can be formed by conveying the integrated hydrophilic fiber layer and synthetic fiber layer by any desired conveying means, while pressing against them a plurality of cutting blades provided on the peripheral surface of a rotating cutting roll, from above the synthetic fiber layer. By adjusting the clearance between the cutting blades of the cutting roll and the conveying means, it is possible to form slits that do not penetrate through the hydrophilic fiber layer.

Also, the direction in which the plurality of notched sections and slits extend is not limited to being parallel to the widthwise direction $D_W$ of the absorbent article, and for example, it may be a direction that forms an angle of 0° to less than 45° with the widthwise direction $D_W$ of the absorbent article, in a plane view. The phrase "an angle of 0° to less than 45° with the widthwise direction $D_W$ of the absorbent article", as used herein, means that the smallest angle of the angles formed between a straight line parallel to the widthwise direction $D_W$ of the absorbent article, and the notched sections and slits, is an angle of 0° to less than 45°. If the angle formed between the direction in which the notched sections and slits extend and the widthwise direction $D_W$ of the absorbent article is 45° or greater, the fibers oriented in the widthwise direction $D_W$ of the absorbent article in the hydrophilic fiber layer will be more prone to breakage when the notched sections and slits are formed, thus potentially lowering the strength in the widthwise direction of the hydrophilic fiber layer.

The shapes of the notched sections and slits in a plane view in the absorbent article of the present invention are not limited to being straight linear as described above, and any desired shape may be employed within a range that does not reduce the ease of deformation of the absorbent body or the strength of the absorbent body. Such shapes include, for example, curves, V-shapes, wavy forms, zigzag shapes, circular shapes and polygonal shapes.

Also, as shown in FIG. 3, the hydrophilic fiber layer 5 of this embodiment has a plurality of recesses 9 on the side opposite the side with the slits 8, at locations corresponding to the plurality of slits 8 in the thickness direction. When such a plurality of recesses are formed in the hydrophilic fiber layer, since deformation is facilitated at the plurality of recesses, the absorbent article has excellent flexibility, and a comfortable feel during wear can be provided for the wearer.

In the absorbent article of the present invention, the structures of the recesses are not particularly restricted so long as the ease of folding of the absorbent body is not impaired, but from the viewpoint of ease of deformation along the shape of the body, the lengths of the recesses may be 3 mm to 60 mm, for example, and are preferably 5 mm to 20 mm. The widths of the recesses are also not particularly restricted but may be 0.1 mm to 5 mm, for example, and are preferably 0.5 mm to 2 mm. If the widths of the recesses are within this range, they will more easily function as origins during folding of the absorbent body.

The depths of the recesses in the absorbent article of the present invention are not particularly restricted but may be, for example, 0.05 mm to 5 mm and are preferably 0.1 mm to 3 mm, from the viewpoint of easier folding of the absorbent body. Throughout the present description, the recess depth is the distance between the side of the hydrophilic fiber layer opposite the side having the slits, and the maximum depth of a recess, and it can be determined by the same measuring method as for the slit depth. That is, in the method of measuring the slit depth described above, the distance (mm) from the imaginary bottom face to the maximum depth of the recess is measured, and the average of the measured values of the distances obtained for 10 arbitrary recesses is recorded as the recess depth (mm).

In the absorbent article of the present invention, the total depth of the slit and notched section is preferably greater than the recess depth. If the total depth of the slit and notched section is greater than the recess depth, the absorbent body will fold to the side having the slits and notched sections, making it possible to prevent exposure of pulp and the like in the hydrophilic fiber layer by the slits, and allowing the durability of the absorbent body to be improved as a result. Incidentally, the total depth of the slit and notched section can be measured in the same manner as for the slit depth described above.

The shapes of the recesses in the absorbent article of the present invention in a plane view are not particularly restricted, but they preferably have essentially the same shapes as the slits. If the slits and recesses have essentially the same shapes in a plane view, the absorbent body will be able to precisely fold with the sections between the slits and recesses as origins. Throughout the present description, "essentially the same shapes" means that the shapes are of the same type, such that the center lines of the shapes overlap.

The plurality of recesses in the absorbent article of the present invention can be easily formed by compressing means such as embossing. When the recesses are formed by compressing means such as embossing, the sections between the bottom parts of the non-through slits and the recesses become compressed and highly densified in the thickness direction of the hydrophilic fiber layer, producing a difference in rigidity between the densified sections and the surrounding sections, such that the hydrophilic fiber layer easily folds with the densified sections as origins, and the absorbent article easily deforms along the body shape of the wearer. Furthermore, the increased density at the sections between the bottom parts of the slits and recesses reinforces the regions of the absorbent body that have the slits, thereby allowing the durability of the absorbent body to be improved as well.

The compressing means may be also be used in combination with the means for forming the notched sections and slits. That is, the recesses may be formed simultaneously with the notched sections and slits. A method of simultaneously forming the notched sections, slits and recesses in the absorbent body includes a step (a) in which the integrated hydrophilic fiber layer 5 and synthetic fiber layer 6 are conveyed by any desired conveying means, a step (b) in which the hydrophilic fiber layer 5 and synthetic fiber layer 6 are conveyed while pressing against them a plurality of cutting blades from above the synthetic fiber layer 6, to form a plurality of through notched sections 7 and non-through slits 8 in the synthetic fiber layer 6 and hydrophilic fiber layer 5, respectively, and a step (c) in which the cutting blades are removed from the hydrophilic fiber layer 5 and synthetic fiber layer 6.

In this method, a plurality of through notched sections 7 and non-through slits 8 are formed in step (b), during which time the pressing force of the cutting blades causes the sections between the bottom parts of the non-through slits 8 and the conveying means to become compressed, forming highly densified sections HD as shown in FIG. 3, while the hydrophilic fiber layer 5 is deformed into protrusions on the lower side centering around the points of contact of the cutting blades (i.e., the bottom parts of the slits 8). When the pressing force of the cutting blades is removed in step (c), the hydrophilic fiber layer 5 deformed in this manner is restored to the original shape by the elastic force of the fibers composing the hydrophilic fiber layer 5; however, the highly densified sections HD between the bottom parts of the non-through slits 8 and the conveying means, being compressed, are not restored and the state of the highly densified sections HD adjacent to the bottom parts of the slits 8 is maintained, such that recesses 9 are formed on the conveying means side of the hydrophilic fiber layer 5 (i.e., the side opposite from the side having the slits 8), centering around the highly densified sections HD.

Since this method allows simultaneous formation of a plurality of notched sections and slits and a plurality of recesses in a single step, it is possible to more efficiently render the absorbent article flexible, and since the slits and recesses are formed with essentially the same shapes in a plane view, at corresponding locations in the thickness direction of the absorbent body, it is possible to precisely fold the absorbent body at the sections between the bottom parts of the slits and the recesses (i.e., the highly densified sections HD) as origins, to provide a comfortable feel during wear for the wearer. Furthermore, since the highly densified sections HD are formed between the bottom parts of the non-through slits and the recesses, it is possible to obtain the same effect as when compressing means such as embossing is used.

The means for forming the recesses is not limited to the means described above, and for example, the recesses can also be easily formed by creating low basis weight regions at prescribed sections of the hydrophilic fiber layer.

The present invention can be applied not only to a sanitary napkin according to the embodiment described above, but also to various types of absorbent articles, such as panty liners and incontinence pads. Furthermore, the absorbent article of the present invention is not restricted to the embodiment described above and can be appropriately modified within a range that is not outside of the object and gist of the present invention.

REFERENCE SIGN LIST

1 Napkin (absorbent article)
2a, 2b Side section sheets
3 Top sheet
4 Absorbent body
5 Hydrophilic fiber layer
6 Synthetic fiber layer
7 Notched section
8 Slit
9 Recess

The invention claimed is:

1. An absorbent article including a liquid-permeable top sheet, a liquid-impermeable back sheet, and an absorbent body situated between the top sheet and the back sheet, wherein
the absorbent body includes at least a hydrophilic fiber layer having a plurality of non-through slits and including hydrophilic fibers,
the hydrophilic fiber layer has, on a side opposite a side with the slits, a plurality of recesses at locations corresponding to the plurality of non-through slits, in a thickness direction of the absorbent article, and
the absorbent body comprises a synthetic fiber layer that is adjacent to the hydrophilic fiber layer and is made of synthetic fibers, the synthetic fiber layer having notched sections that communicate with the slits, at locations corresponding to each of the slits of the hydrophilic fiber layer in the thickness direction.

2. The absorbent article according to claim 1, wherein the slits and recesses have essentially same shapes, in a plane view.

3. The absorbent article according to claim 1, wherein a total depth of the slit and notched section is greater than a recess depth.

4. The absorbent article according to claim 1, wherein the synthetic fiber layer comprises a nonwoven fabric.

5. The absorbent article according to claim 1, wherein the hydrophilic fiber layer and the synthetic fiber layer are joined.

6. The absorbent article according to claim 1, wherein the hydrophilic fiber layer and the synthetic fiber layer are joined by a hot-melt adhesive.

7. The absorbent article according to claim 1, wherein the synthetic fiber layer is adjacent to skin side of the hydrophilic fiber layer.

8. The absorbent article according to claim 1, wherein a fiber density of portions between bottom parts of the slits and the recesses are higher than a fiber density of other parts.

9. The absorbent article according to claim 1, wherein the synthetic fiber layer is in direct contact with the hydrophilic fiber layer.

10. The absorbent article according to claim 1, wherein
the notched sections of the synthetic fiber layer extend all the way through the synthetic fiber layer in the thickness direction, and
the notched sections of the synthetic fiber layer and the slits of the hydrophilic fiber layer are spatially connected.

11. The absorbent article according to claim 10, wherein each of the notched sections has a linear shape with a length in a range of 3 mm to 50 mm.

12. The absorbent article according to claim 10, wherein a depth of each of the slits in the thickness direction is in a range of 0.05 mm to 5.0 mm.

13. The absorbent article according to claim 1, wherein
the absorbent body includes a transverse direction and a longitudinal direction perpendicular to each other, the transverse direction and longitudinal direction being perpendicular to the thickness direction of the absorbent body, and
each of the notched sections and slits is elongated in the transverse direction of the absorbent body.

* * * * *